United States Patent
Doktycz et al.

(10) Patent No.: US 6,627,157 B1
(45) Date of Patent: Sep. 30, 2003

(54) DUAL MANIFOLD SYSTEM AND METHOD FOR FLUID TRANSFER

(75) Inventors: Mitchel J. Doktycz, Knoxville, TN (US); William Louis Bryan, Knoxville, TN (US); Reid Kress, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/262,455

(22) Filed: Mar. 4, 1999

(51) Int. Cl.[7] .............................. B01L 3/02; G01N 1/10; G01N 1/14
(52) U.S. Cl. .................... 422/100; 436/180; 73/864; 73/864.01; 73/864.11; 73/864.02; 73/863.32; 73/864.17
(58) Field of Search .................. 422/100; 73/864.17, 73/863.32, 864, 864.01, 864.02, 864.11; 436/180

(56) References Cited

U.S. PATENT DOCUMENTS

| | | | | |
|---|---|---|---|---|
| 4,199,013 A | * | 4/1980 | Reich | 141/130 |
| 4,353,243 A | * | 10/1982 | Martin | 73/23.1 |
| 4,432,470 A | * | 2/1984 | Sopha | 222/135 |
| 4,621,665 A | * | 11/1986 | Webb | 141/1 |
| 4,748,002 A | * | 5/1988 | Neimark et al. | 422/116 |
| 4,809,909 A | * | 3/1989 | Kukesh | 239/1 |
| 5,092,184 A | * | 3/1992 | Goodell et al. | 73/863.32 |
| 5,316,181 A | * | 5/1994 | Burch | 222/61 |
| 5,338,688 A | | 8/1994 | Deeg et al. | |
| 5,348,606 A | * | 9/1994 | Hanaway et al. | 156/292 |
| 5,545,531 A | | 8/1996 | Rava et al. | |
| 5,704,399 A | * | 1/1998 | Hayashi et al. | 137/884 |
| 5,728,351 A | * | 3/1998 | Carver, Jr. | 422/73 |
| 5,741,554 A | * | 4/1998 | Tisone | 427/424 |
| 5,807,522 A | | 9/1998 | Brown et al. | |
| 5,838,340 A | | 11/1998 | Simoda | |
| 5,855,713 A | | 1/1999 | Harvey | |
| 5,862,832 A | * | 1/1999 | Victor et al. | 137/606 |
| 5,964,089 A | * | 10/1999 | Murphy et al. | 60/286 |
| 5,988,236 A | * | 11/1999 | Fawcett | 141/130 |
| 6,033,911 A | * | 5/2000 | Schultz et al. | 436/49 |
| 6,079,283 A | * | 6/2000 | Papen et al. | 73/864.11 |
| 6,083,761 A | * | 7/2000 | Kedar et al. | 436/178 |
| 6,083,762 A | * | 7/2000 | Papen et al. | 436/180 |
| 6,106,783 A | * | 8/2000 | Gamble | 422/102 |
| 6,152,162 A | * | 11/2000 | Balazy et al. | 137/110 |
| 6,159,629 A | * | 12/2000 | Gibb et al. | 429/39 |
| 6,212,949 B1 | * | 4/2001 | Inder et al. | |
| 6,231,739 B1 | * | 5/2001 | Nordman et al. | |
| 6,254,826 B1 | * | 7/2001 | Acosta et al. | |
| 2001/0005489 A1 | * | 6/2001 | Roach et al. | |
| 2001/0016178 A1 | * | 8/2001 | Acosta et al. | |

FOREIGN PATENT DOCUMENTS

| | | |
|---|---|---|
| DE | 19712195 | 9/1998 |
| FR | 2 317 634 | 4/1977 |
| WO | WO 98/29736 | 7/1998 |
| WO | WO 99/55460 | 11/1999 |

OTHER PUBLICATIONS

Le, Hue, "Progress and Trends in Ink–Jet Printing," *Journal of Imaging Science and Technology*, vol. 42, No. 1, Jan./Feb. 1998.

* cited by examiner

Primary Examiner—T. Tung
Assistant Examiner—Brian R Gordon
(74) Attorney, Agent, or Firm—Akerman Senterfitt

(57) ABSTRACT

A dual-manifold assembly is provided for the rapid, parallel transfer of liquid reagents from a microtiter plate to a solid state microelectronic device having biological sensors integrated thereon. The assembly includes aspiration and dispense manifolds connected by a plurality of conduits. In operation, the aspiration manifold is actuated such that the aspiration manifold is seated onto an array of reagent-filled wells of the microtiter plate. The wells are pressurized to force reagent through conduits toward the dispense manifold. A pressure pulse provided by a standard ink-jet printhead ejects nanoliter-to-picoliter droplets of reagent through an array of printhead orifices and onto test sites on the surface of the microelectronic device.

20 Claims, 7 Drawing Sheets

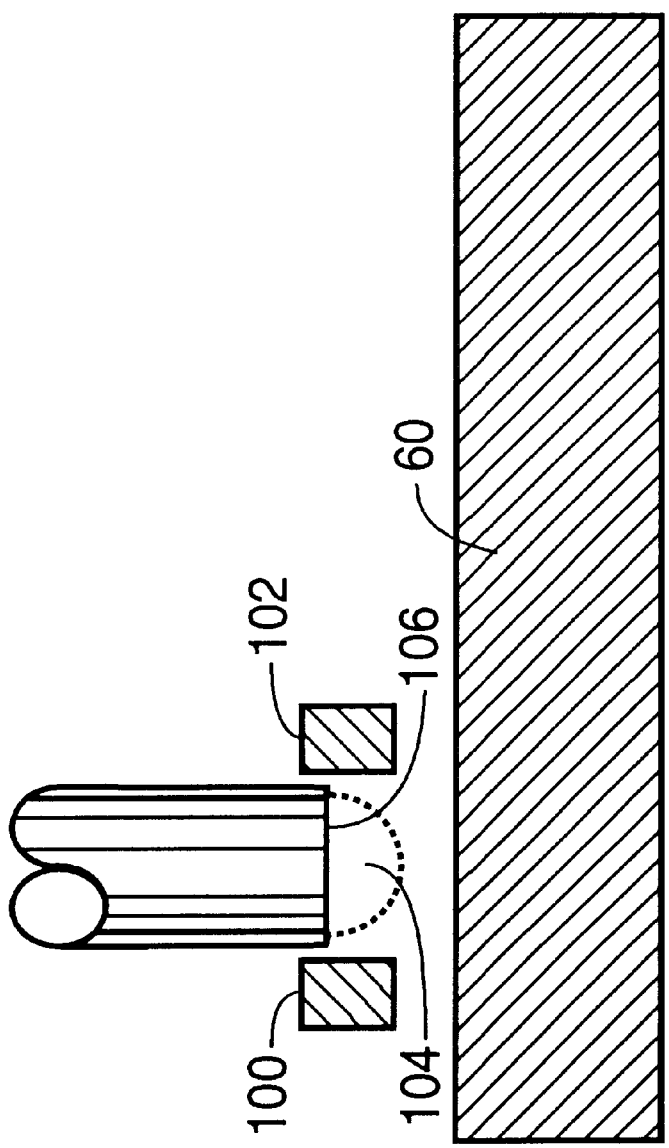

DUAL MANIFOLD SYSTEM AND METHOD FOR FLUID TRANSFER

STATEMENT REGARDING FEDERALLY-SPONSORED RESEARCH OR DEVELOPMENT

This invention was made with government support under contract DE-AC05-96OR22464, awarded by the United States Department of Energy to Lockheed Martin Energy Research Corporation, and the United States Government has certain rights in this invention.

FIELD OF THE INVENTION

This invention relates generally to an apparatus and method for fabricating microarrays of biological samples on a support substrate, and more particularly to a dual manifold system for the rapid, parallel transfer of reagents to test substrates for large-scale screening assays.

BACKGROUND OF THE INVENTION

In clinical chemistry, it is frequently necessary to carry out the metered application of an analytical liquid to a target. One case which is particularly relevant to the present invention is the application of the analytical liquid to an analysis element such as a chip-based biological sensor in which biological materials are integrated with microelectronic devices. In recent years, rapid technological advances have enabled the use of micro-scale chemical/biochemical reactions for performing various types of analyses. For instance, DNA microarrays such as genosensors allow thousands of samples to be assessed simultaneously on a microelectronic test chip that is less than one-quarter of an inch in length per side. Typical test sites on such a chip are on the order of about 100 microns ($\mu$m) in diameter. Conventional applications of chip-based biological sensors include mutation diagnosis, organism identification and gene expression profiling. More recent applications, such as parallel screening of chemical compounds for drug discovery and protein arrays for functional analysis, will soon be routine.

Known fluid handling systems for dispensing, or "micro-spotting", arrays of biological materials on a target substrate commonly comprise pick-and-place equipment. Generally, pick-and-place dispense systems include a dispense head adapted for transferring volumes of fluid from a fluid source to a target substrate. The time required to pick up, transfer and deposit a given volume of liquid significantly limits the efficiency of pick-and-place systems for micro-spotting. This lack of efficiency is even more pronounced where the target substrate contains hundreds, or even thousands, of test sites. Efforts have been made to improve the efficiency of pick and place systems for micro-spotting. For instance, systems have been adapted for picking up, transferring and depositing multiple sample volumes simultaneously. However, the time required for dispense head movement remains a significant limitation of such systems.

Furthermore, the multiple degrees of freedom associated with the movement of individual system components, such as the dispense head, significantly limits the positional accuracy of samples deposited on a target substrate. In instances where the equipment is adapted for contact dispensing (i.e., where the dispense elements of the system physically contact the target substrate to effect transfer of the fluid to the target substrate) such limitations may be magnified. In particular, dispense tip deformation can lead to irregular sample spacing and, in some instances, cross-contamination of adjacent test sites.

Due in part to the aforementioned limitations, the positional accuracy and liquid transfer volume capability of conventional pick-and-place dispensing systems can not meet the requirements of many evolving applications. Constructing microarrays having a higher degree of miniaturization will require an increase in test site array density. Realizing such an increase in density will require a reduction in sample spot size and spot pitch (i.e., the center-to-center distance between adjacent deposits). In order to achieve such miniaturization, a fluid handling system capable of accurately and efficiently depositing chemical and biochemical reagent droplets having volumes on the order of picoliters is required.

Technology for dispensing liquid volumes on the order of picoliters exists, but has been primarily limited to the field of ink-jet printing. Many drop-on-demand ink-jet ideas and systems were invented, developed, and produced commercially in the 1970s and 1980s. A detailed and comprehensive summary of state-of-the-art drop-on-demand ink-jet printing technologies, including the fabrication of ink-jet valves and printheads, is provided in a published article by Hue P. Le, entitled Progress and Trends in Ink-jet Printing (Journal of Imaging Science and Technology, Volume 42, Number 1, pp. 49–62)(1998).

There is an established need for an apparatus and method for accurately and efficiently transferring and depositing, or printing, microarrays of reagent samples having volumes on the order of picoliters on a test substrate. It would be desirable to have a microarray printing apparatus for performing large-scale chemical/biochemical screening assays, wherein the system incorporates known drop-on-demand ink-jet printing technology and is particularly suited for dispensing chemical and/or biochemical reagents.

SUMMARY OF THE INVENTION

It is an object of this invention to provide a liquid transfer apparatus capable of accurately and efficiently transferring liquid reagents from an array of reservoirs to an array of sites on a target substrate It is another object of this invention to provide a liquid transfer apparatus capable of accurately and efficiently depositing volumes of liquid reagents in the range of about $(10)^{-12}$ to about $(10)^{-6}$ liters.

It is another object of this invention to provide a liquid transfer apparatus capable of effecting such reagent transfer with minimal movement of the apparatus during operation.

It is another object of this invention to provide a liquid transfer apparatus employing non-contact dispensing.

It is another object of this invention to provide a liquid transfer apparatus and method adapted for the automated printing, or micro-spotting, of multiple analytical chips in succession for performing large-scale screening assays.

These and other objects are achieved with the assembly and method of the present invention. Briefly, according to the invention, a dual-manifold assembly generally includes an aspiration manifold 10, a dispense manifold 20, and fluid transfer elements 80 for the parallel transfer of fluids therebetween. Although the apparatus and method are adaptable for use transferring a variety of liquids to a variety of target substrates, in the preferred embodiment of the invention the apparatus is particularly suited for transferring chemical or biochemical reagents from an array of microtiter plate wells to an array of test sites on a chip-based biological sensor.

The aspiration manifold 10 is positioned above a source plate 50, such as a microtiter plate, and is adapted for simultaneously aspirating liquid, such as a chemical reagent, from an array of reservoirs 52. In the preferred embodiment of the present invention, the aspiration manifold includes an array of aspiration manifold subassemblies extending through a base plate 17 and adapted for being received by an array of reagent-filled wells 52. When the aspiration manifold is seated onto the microtiter plate 50, each subassembly seals a single well such that fluid communication to and from the well is limited to a pair of conduits 12, 14 extending into the well. In operation, each well is pressurized by a pressure source 40 through conduit 12 which urges the liquid 54 through conduit 14 toward dispense manifold 20. In an alternate embodiment of the invention, the aspiration manifold has a gasket element 23 for sealing against the periphery of the microtiter plate 50 during operation, precluding the need to pressurize the wells individually. In this alternate embodiment, pressurization of the wells 52 is accomplished through a single pressure conduit 12 extending through base plate 17.

In the preferred embodiment of the invention, a plurality of aspiration conduits communicate with the dispense manifold side of the assembly through a modular connector 90. Generally, the modular connector includes a male component 94 which releasably engages a female component 92. Preferably, the aspiration conduits 14 terminate at component 94 which has integral tips 95 adapted for receipt by female component 92. Preferably, the female component 92 of the modular connector is integrated into valve assembly 21. Conduits 24, 26 and 38, of valve assembly 21, can also be adapted for modular connection with other subassemblies of the dual manifold system. For instance, although dispense manifold 20 can be directly integrated into valve assembly 21, in the preferred embodiment of the invention dispense manifold 20 is adapted for modular connection to valve assembly 21.

Volumes of reagent in the range of about $(10)^{-12}$ to about $(10)^{-6}$ liters are ejected from the dispense manifold through an array of dispense manifold orifices 106 upon application of a force, such as a pressure pulse. Preferably, a pressure pulse is provided by a valve 28 incorporating ink jet style drop-on-demand technology. Valve 28 may be adapted for modular connection to valve assembly 21 or, alternatively, valve 28 may be directly integrated into the valve assembly. In the preferred embodiment of the invention, the dispense manifold 20 comprises a standard ink-jet style printing head having micro-machined channels each terminating at an orifice 106.

In an alternate embodiment of the invention, a purging apparatus 30 is provided for periodically purging the assembly. Purging apparatus 30 includes gas and cleaning liquid inlets, 32 and 34 respectively, controllable through a solenoid or other suitable valve 36. Preferably, purging apparatus 30 is adapted for modular connection to valve assembly 21. Alternatively, apparatus 30 can be directly integrated into the valve assembly.

In further embodiments of the invention, auxiliary features are included for improving registration and alignment of reagent samples deposited on the test chip. In particular, fiducial pins and/or marks are integrated into the target substrate. The integrated features are sensed by a conventional vision system for ensuring proper alignment and orientation during operation.

In yet a further embodiment of the invention, detection means are provided for detecting the passage of a droplet 104 of reagent from a dispense orifice 106. The detection means may comprise optoelectronic devices, such as a photodiode 100/photodetector 102 pair positioned near each orifice. Alternatively, electronic conduction-based sensors can be integrated into the dispense manifold.

In operation, microtiter plate 50 is positioned below the aspiration manifold 10 and the aspiration manifold is subsequently seated onto the plate such that an air-tight seal is formed between the aspiration manifold and the plate. Microtiter plate wells 52 are pressurized by a pressure source 40 through at least one conduit 12 to effect the transfer of reagent through a plurality of conduits 14 and into dispense manifold 20 positioned above target substrate 60. Subsequently, a pressure pulse from valve 28 is communicated to the dispense manifold 20, effecting the transfer of a desired volume of reagent through orifice 106 to test sites 64 on target substrate 60. Further embodiments of the method include aligning the target substrate to ensure proper positioning of the reagent deposits, detecting the passage of reagent samples from the orifices of the dispense manifold, and purging the system between deposition, or printing, operations.

BRIEF DESCRIPTION OF THE DRAWINGS

FIG. 7 is a cross-sectional view of a droplet ejection detection apparatus in accordance with an alternate embodiment of the present invention.

DETAILED DESCRIPTION OF THE PREFERRED EMBODIMENTS

Figure 1:
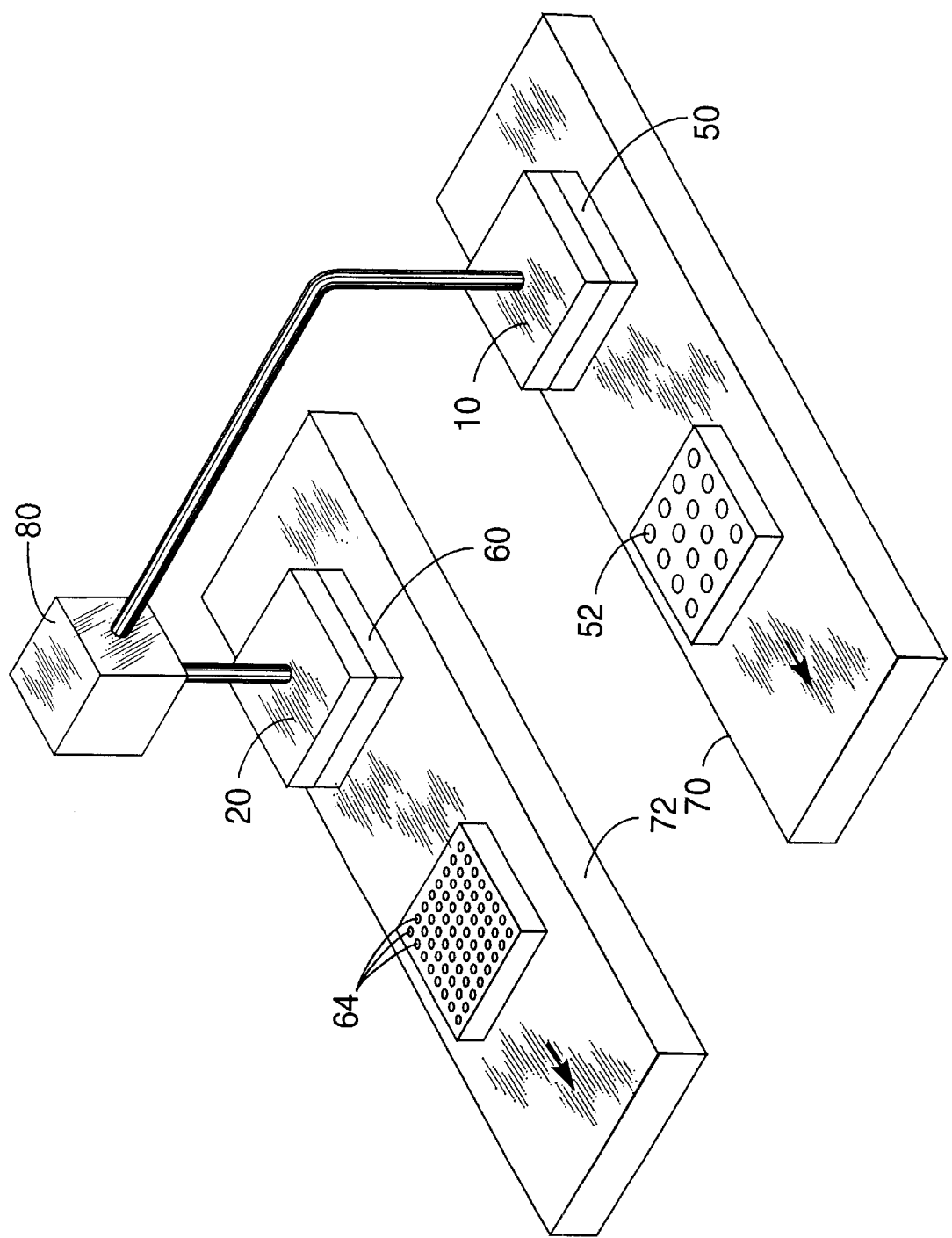
FIG. 1 is a schematic of the major components of a dual manifold assembly in accordance with the present invention.
Figure 2:
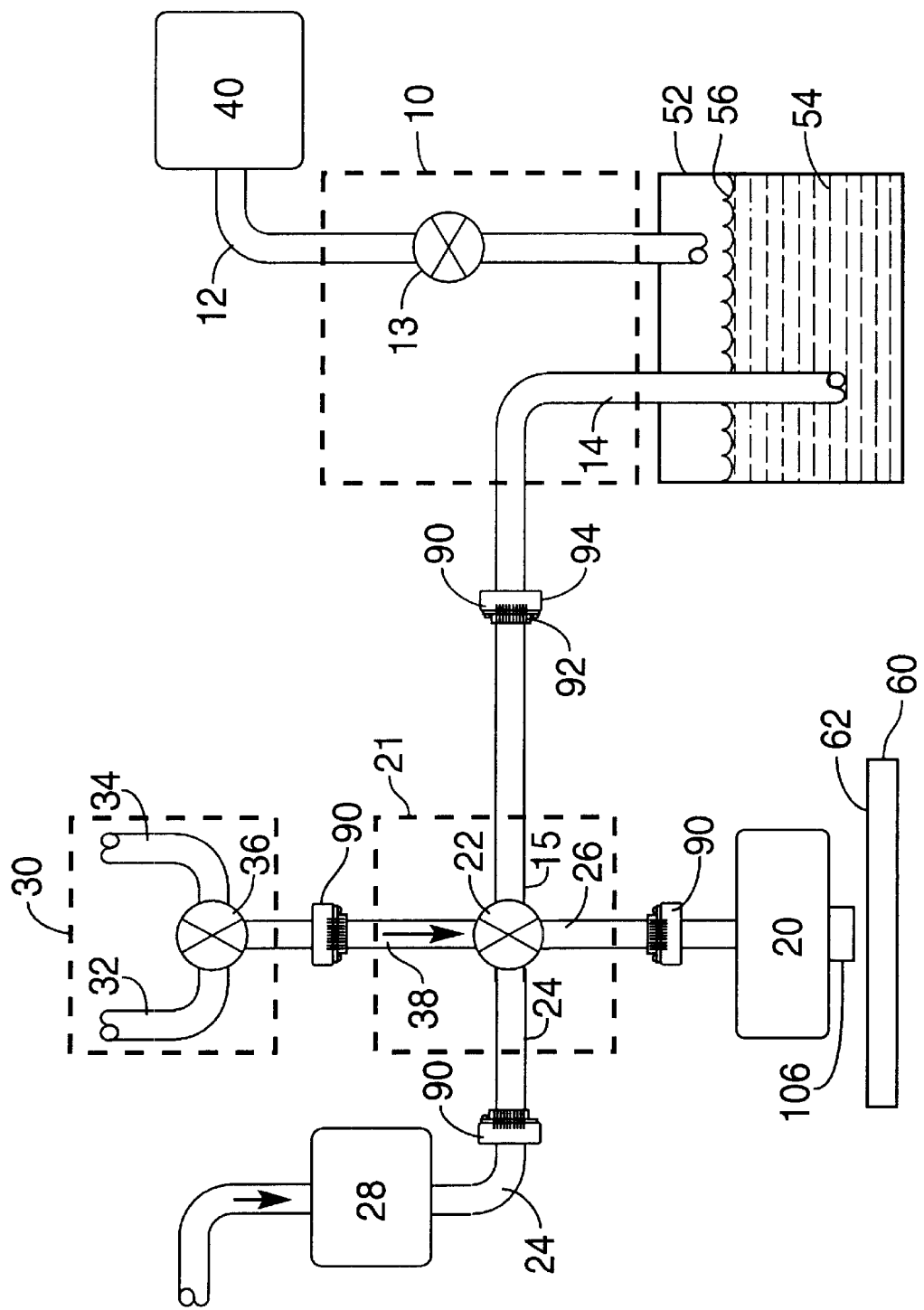
FIG. 2 is a schematic of a particular arrangement of subcomponents of a dual-manifold assembly in accordance with a preferred embodiment of the present invention.

Referring now to FIGS. 1 and 2, a dual manifold assembly is provided for the rapid, parallel transfer of liquid from an array of reservoirs 52 to a target substrate 60. It will be apparent to one skilled in the art of microarray printing that the apparatus of the present invention lends itself to a variety of applications. Generally, the assembly is capable of transferring liquids from virtually any type of reservoir—including tubes, bottles and other liquid containers—to virtually any type of substrate. However, in the preferred embodiment of the present invention the assembly is particularly suited for transferring chemical or biochemical reagents from an array of wells 52 of a conventional microtiter plate to an array of test sites 64 on a chip-based biological sensor (commonly referred to in the art as a "microarray") for performing screening assays. The assembly is adaptable for printing arrays wherein the distance between adjacent test sites, or test site pitch, is in the range of about 1 micron ($\mu$m) to about 10,000 microns ($\mu$m).

The assembly includes aspiration and dispense manifolds, 10 and 20 respectively, separated by fluid transfer elements (generally denoted by reference numeral 80). In operation, the dual-manifold assembly is adapted for the automated printing of multiple analytical chips in succession. Preferably, a conventional microtiter plate feeder 70 is employed for advancing a series of microtiter plates beneath the aspiration manifold 10, and a target chip track 72 is employed for advancing test substrates 60 beneath the dispense manifold 20. Although the term "advancing" is used to describe movement of the tracks 70, 72, the invention is not intended to be so limited. In particular, either or both of the tracks can be adapted for movement in multiple directions.

In the preferred embodiment of the invention, the assembly is adapted for transferring reagent from a given number of reservoirs 52 to an equal number of test sites 64 and, accordingly, the assembly is designed for the one-to-one transfer of liquid, i.e., from each reagent reservoir to a designated test site. However, the flexibility of the present invention lends itself to numerous variations of the preferred use. In particular, the assembly can be configured for transferring liquid from a given number of reservoirs to a different number of test sites. For instance, the dispense manifold 20 can be designed such that liquid samples from multiple aspiration reservoirs are combined and dispensed on a single test site. Conversely, the manifolding can be adapted for depositing liquid from a single reservoir to multiple test sites.

A preferred embodiment of the dual-manifold assembly of the present invention is schematically illustrated in FIG. 2. Although the assembly is adapted for simultaneously transferring multiple volumes of liquid reagent to multiple chip test sites, a clearer understanding of the invention can be gained through a description of the operation of the assembly with respect to the transfer of reagent from a single reservoir 52 to a single test site on target substrate surface 62. Accordingly, FIG. 2 intentionally depicts a single set of fluid transfer elements. A pneumatic source 40 provides controlled pressure to reservoir 52 through a conduit 12 extending into the reservoir, with conduit 12 terminating at a position above liquid level 56. The magnitude and duration of the pressure supplied to the reservoir can be adjusted by aspiration manifold valve 13. Valve 13 is preferably a solenoid valve; however, other suitable valves are contemplated. For instance, other suitable valves may include shear valves, flat face valves and pinch valves, actuated by mechanical, electrical or pneumatic means. Upon application of pressure to the reservoir, liquid 54 is urged into and through aspiration conduit 14. In the preferred embodiment of the invention, conduits 12 and 14 comprise narrow-bore plastic tubing having an inner diameter preferably ranging from about 0.020 mm to about 2.0 mm. However, the conduits can be manufactured from other suitable materials capable of transferring the desired fluids without being degraded, including, but not limited to, metals and glass.

In the preferred embodiment of the present invention, the aspiration manifold and dispense manifold sides of the assembly communicate through at least one modular fluid connector 90. In particular, aspiration conduits 14 are bundled together and combined in a male component, or plug 94, adapted for releasably engaging a female connector portion 92. Alternatively, as will be apparent to one skilled in the art, the aspiration conduits could be combined in a female plug adaptable for connection with a male component. The structure of a preferred modular connection is described in more detail below; however, numerous variations are possible without departing from the spirit and scope of the invention. Furthermore, although the modular connector 90 is depicted attached to a conduit 15 extending away from valve assembly 21, it is preferred that the female connector portion 92 is integrated directly into valve assembly 21. In this manner, the assembly of the present invention is adaptable for the simple and efficient attachment to myriad different aspiration manifold designs. In other words, regardless of the structure of the aspiration manifold, the aspiration conduits are combined in a standard connector or plug 94 adapted for releasably engaging female connector portion 92. Thus, by integrating connector 92 into the valve assembly 21, a single valve assembly 21 can be modularly connected to a variety of aspiration manifolds having different geometries, dimensions, and structures.

Valve assembly 21 includes a dispense manifold switching valve 22 which is preferably a flat face valve; however, other suitable valves are contemplated including, but not limited to, shear valves, solenoid valves and pinch valves, actuated by mechanical, electrical or pneumatic means. Switching valve 22 is fluidly connected to an ejection means 28 for advancing liquid through channels (not shown) in the dispense manifold 20, to effect the ejection of a desired volume of the liquid onto the test substrate. Preferably, the ejection means delivers a pressure pulse having a pressure ranging from about $6.9(10)^3$ N/m$^2$ to about $138(10)^3$ N/m$^2$, and having a duration ranging from about $(10)^{-6}$ seconds to about $(10)^{-2}$ seconds. In the preferred embodiment of the invention, the ejection means 28 comprises a conventional ink-jet style printing valve or pump designed for drop-on-demand printing. Ink-jet style printing valves/pumps for drop-on-demand printing, including thermal, solenoid and piezoelectric types, are commercially available and well known in the art. For instance, the Lee Company of Essex, Connecticut manufactures a solenoid-based ink-jet valve (Model No. INKX0502600AB) which is suitable for use with the present invention. Although ejection means 28 is shown connected to valve assembly 21 via a conduit 24, the ejection means can be adapted for releasable attachment to the valve assembly, via a modular connector 90, in a manner similar to the preferred aspiration manifold connection. Furthermore, alternate valve arrangements are possible. For instance, an ink jet valve/pump 28 can be directly integrated into valve assembly 21 via conduit 26.

The incorporation of ink-jet drop-on-demand printing technology into the dispense assembly of the present invention provides significant advantages vis-a-vis known systems for printing microarrays. In particular, the ability to deliver the short-duration pressure pulses associated with ink-jet print valves enables the non-contact delivery of reagent sample volumes in the range of about $(10)^{-12}$ to about $(10)^{-6}$ liters. Upon application of a pressure pulse, at least one droplet of reagent is ejected through dispense manifold orifice 106 onto surface 62 of test substrate 60. As used herein, the term "non-contact" refers to the lack of contact between the dispense manifold and the target substrate during deposition. In the preferred embodiment of the invention, liquid is communicated through channels micromachined into an ink-jet style printhead—such as those commonly used in desktop and industrial printers—and each terminating at an orifice 106. Depending upon the particular application, the orifices 106 can have diameters ranging from a minimum of about 1 micron ($\mu$m) to a maximum of about 200 microns ($\mu$m). In the preferred embodiment of the invention, the dispense manifold 20 is adapted for releasable attachment to the valve assembly 21 via a modular connector 90. Furthermore, the modular connector can be integrated directly into switching valve 22. In this manner, the dispense manifold 20 can be fitted with a male connector portion 94 adapted for direct attachment to switching valve 22, precluding the need for conduit 26.

As previously discussed, liquid transferred from a reservoir on the aspiration side of the liquid transfer assembly can be manifolded in such a manner that the liquid is ejected through multiple orifices on the dispense side of the assembly. Conversely, liquid from multiple reservoirs on the aspiration side of the assembly can be combined and ejected through a single dispense orifice. The manifold assembly of the present invention also enables liquid to be transferred from a quantity of reservoirs to a quantity of test sites less than, equal to, or greater than the number of reservoirs. Accordingly, the array of printhead orifices can be dimensioned differently, or arranged in a different pattern, than the array of aspiration conduits 14 extending through the aspiration manifold 10. For instance, the assembly can be adapted for transferring liquid from a non-linear array of reservoirs to a linear array of dispense manifold orifices, and vice-versa. Similarly, the assembly can be adapted for transferring liquid from a rectangular array to a radial array, and vice-versa. As used herein, the term "array" is also intended to encompass a plurality of reservoirs, conduits, orifices or test sites having non-symmetric patterns or variable pitches. The printhead can also be adapted for being rotated during operation. Accordingly, the relative orientations of the aspiration manifold conduits 14 and dispense manifold orifices 106 can be varied.

Significantly, the manifold structure of the present invention enables liquid to be transferred from an array of sample reservoirs having a minimum pitch on the order of millimeters to an array of orifices having a minimum pitch on the order of microns. For instance, we have employed the present invention to transfer reagents from conventional microtiter plate wells having a pitch in the range of about 2.25 mm to about 9.0 mm, to test sites on a solid state substrate having a pitch in the range of about 1 micron to about 10,000 microns.

Auxiliary apparatus 30 may be provided for cleaning and purging the various fluid transfer conduits of the assembly. For example, a gas pressure conduit 32 and cleaning liquid conduit 34 may be fluidly connected, via conduit 38, to switching valve 22. Preferably, the introduction of cleaning/purging fluids into the system is controllable through a suitable valve 36, such as solenoid, shear, flat face and pinch valves, actuated by mechanical, electrical or pneumatic means. Preferably, purging apparatus 30 is fluidly connected to valve assembly 21 through a modular connector 90 integrated into the valve assembly. Alternatively, purging apparatus 30 can be directly integrated into dispense manifold switching valve 22.

Figure 3:
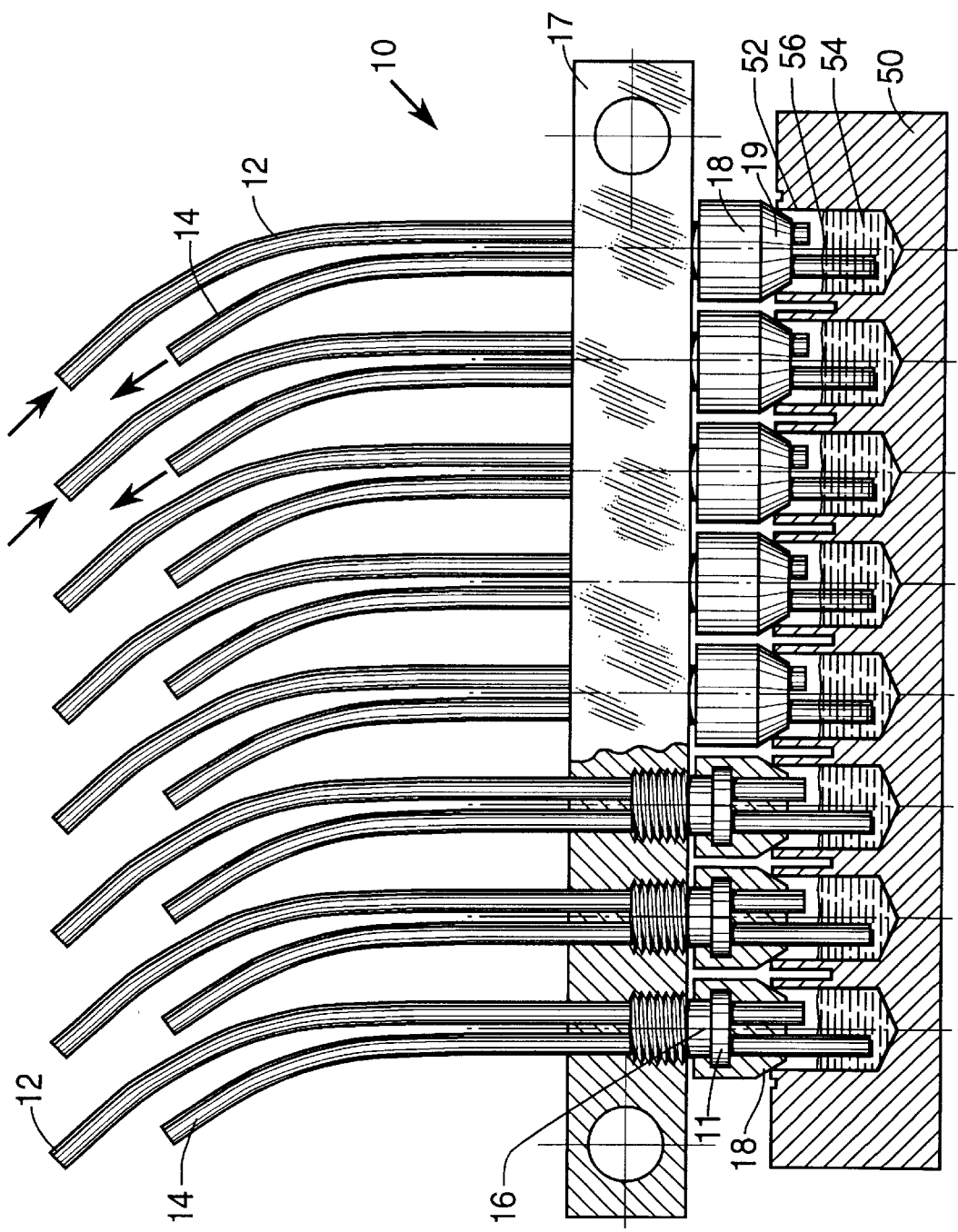
FIG. 3 is a side view, partially in cross-section, of an aspiration manifold in accordance with a preferred embodiment of the present invention.

Referring now to FIG. 3, an aspiration manifold assembly 10 is illustrated in accordance with a preferred embodiment of the present invention. The aspiration manifold includes an array of aspiration subassemblies extending through a base plate 17 and adapted for being received by a corresponding array of liquid filled reservoirs 52 formed in a source plate 50. In the preferred embodiment of the invention, the reservoirs comprise reagent-filled wells formed in a microtiter plate. Each subassembly includes a guide member 16, a cap member 18, a pressure conduit 12 and an aspiration conduit 14. Pressure and aspiration conduits 12 and 14 preferably comprise narrow-bore tubing constructed from plastic, metal or glass. Guide member 16 has a first end adapted for being mechanically fastened to base plate 17. Preferably, mechanical fastening is achieved by providing guide member 16 with a first threaded end for easy mechanical insertion, i.e., twisting, into the base plate. It will be apparent to one skilled in the art that alternate mechanical fastening means are possible. Regardless of the fastening means employed, it is important that the guide member snugly engages the base plate to prevent movement of the guide member during operation of the assembly. When fully inserted, a second flanged end 11 of the guide member extends downward from a lower surface of the base plate. Guide member 16 also has a pair of longitudinally-extending channels (not shown) for snugly-receiving the plastic tubing.

Cap member 18 has a first end adapted for engaging the flanged end 11 of guide member 16. An opposite second end of the cap member has a tapered outer surface 19 for engaging the perimeter of one of the liquid-filled reservoirs 52. Preferably, the cap member is manufactured from a suitable polymer, rubber or other compressible material. In this manner, as aspiration manifold 10 is seated onto microtiter plate 50, the cap members act to seal the reservoirs. Each cap member 18 is provided with longitudinally-extending channels aligning with the channels in a corresponding guide member 16 for receiving the plastic tube conduits. Pressure conduit 12 extends completely through cap member 18, but terminates above liquid level 56. Aspiration conduit 14 extends through cap member 18, terminating at a position below liquid level 56. In operation, aspiration manifold is seated onto microtiter plate 50 such that cap members 18 seal against the perimeter of corresponding wells 52. Subsequently, the wells are pressurized by applying pneumatic pressure through pressure tubing 12, thereby urging the transfer of liquid reagent 54 from the wells 52, through aspiration tubing 14, toward the dispense manifold 20.

Although the various elements of the aspiration manifold assembly are illustrated as individual sub-components, they can be combined. For instance, in an alternate embodiment of the present invention, cap member 18 and guide member 16 comprise a unitary component, for example, molded from plastic or machined from metal. Taking this integration a step further, in yet a further embodiment of the invention, cap and guide members 18 and 16, respectively, are integrated into base member 17 such that the entire aspiration manifold assembly, except for the tubing, comprises a single, unitary component. For instance, the entire aspiration manifold assembly can be molded from a suitable polymer or machined from a suitable metal.

Figure 4:
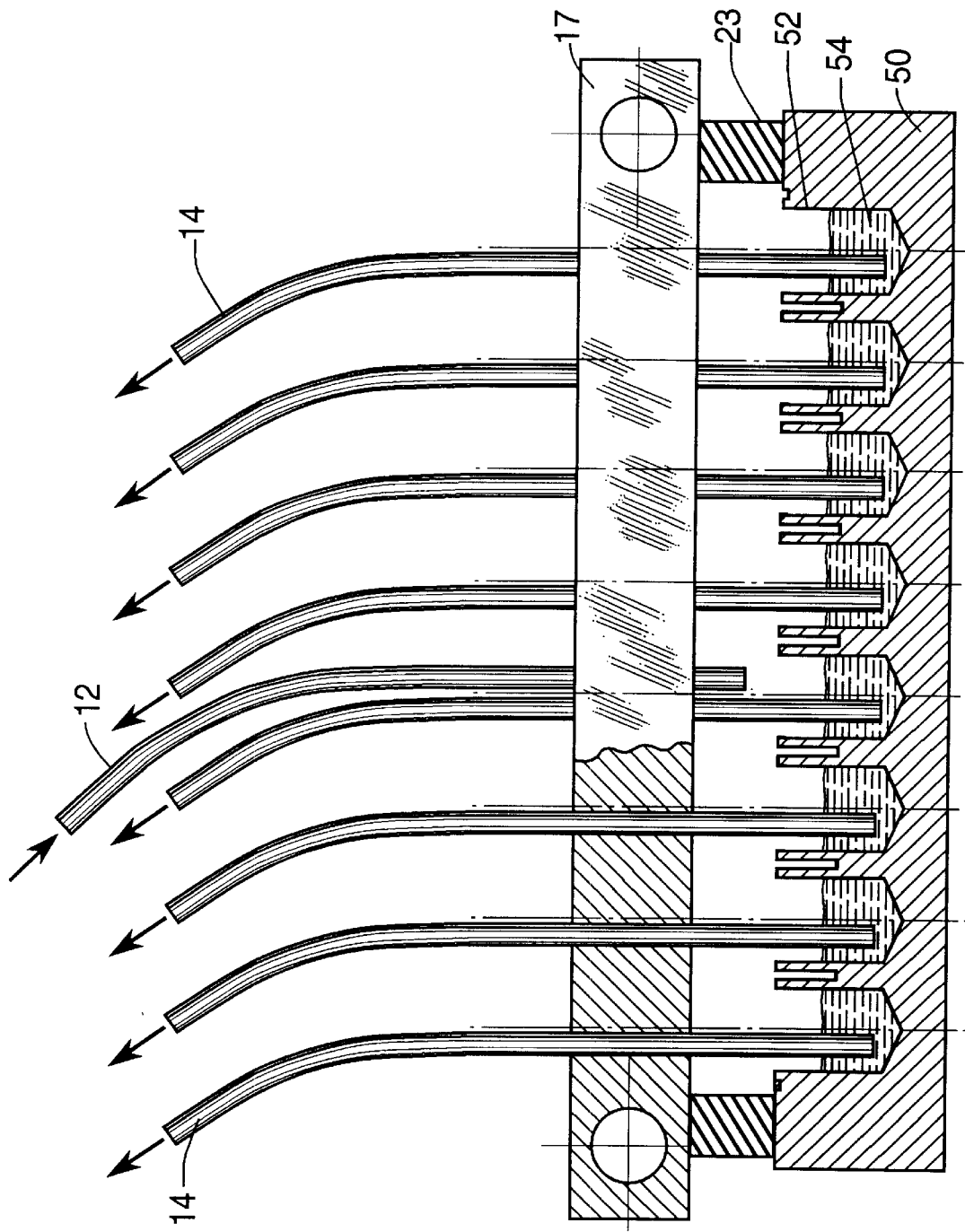
FIG. 4 is a side view, partially in cross-section, of an aspiration manifold in accordance with an alternate embodiment of the present invention.

Referring now to FIG. 4, an alternate embodiment of the aspiration manifold has a single pressure inlet 12 for pressurizing the wells 52. In lieu of individual cap members for sealing each of the wells, a gasket member 23, preferably constructed from a suitable polymer, rubber or other compressible material, is disposed along the periphery of the underside of base plate 17. In this manner, as aspiration manifold 10 is seated onto microtiter plate 50, sealing member 23 seals against the periphery of plate 50. Individual aspiration conduits 14 extend into each of the liquid-filled reservoirs for transferring reagent from the wells to the dispense manifold.

Figure 5:
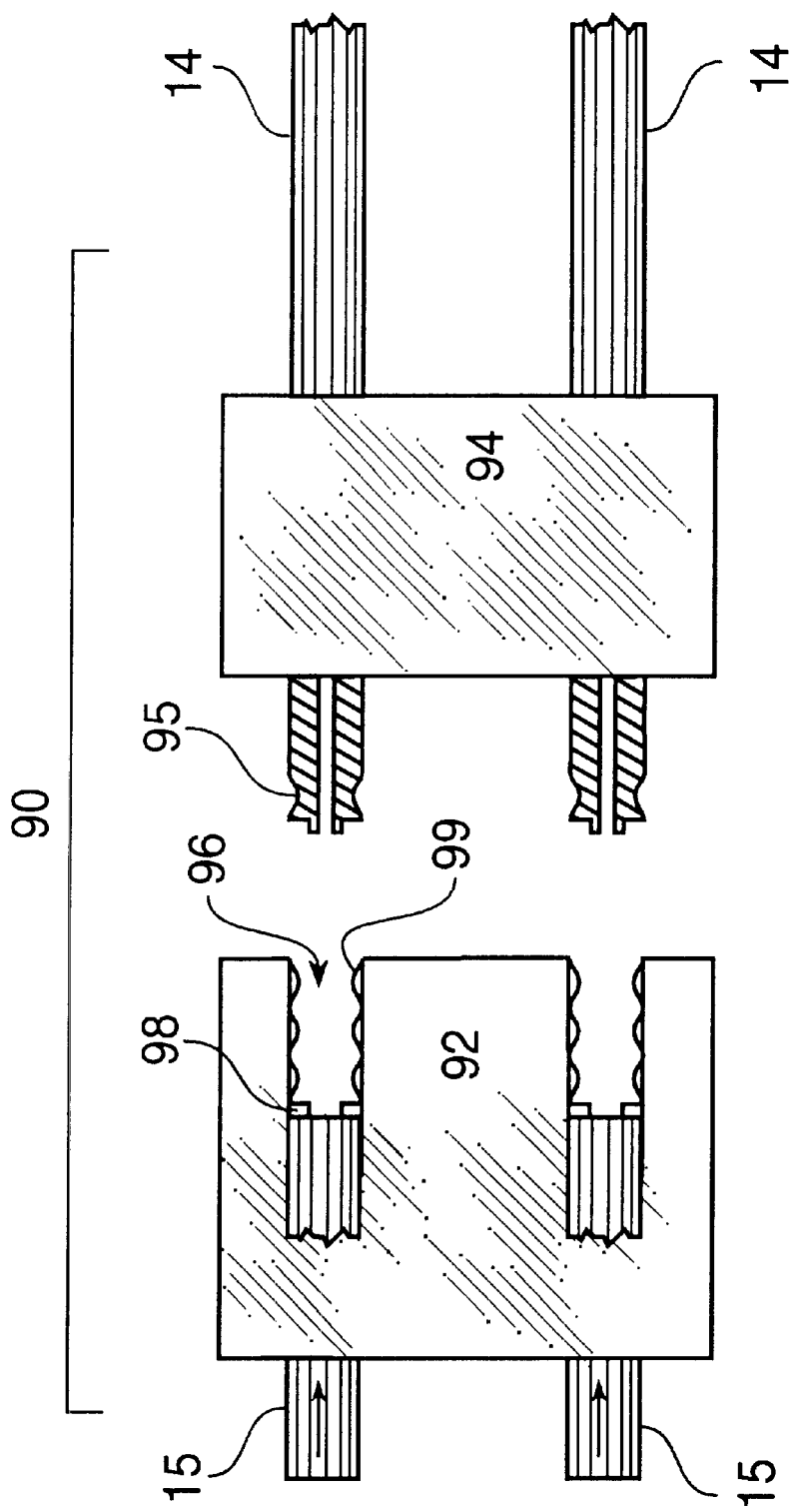
FIG. 5 is a top view, partially cut away, of a preferred modular fluid connector in accordance with the present invention.
Figure 6:
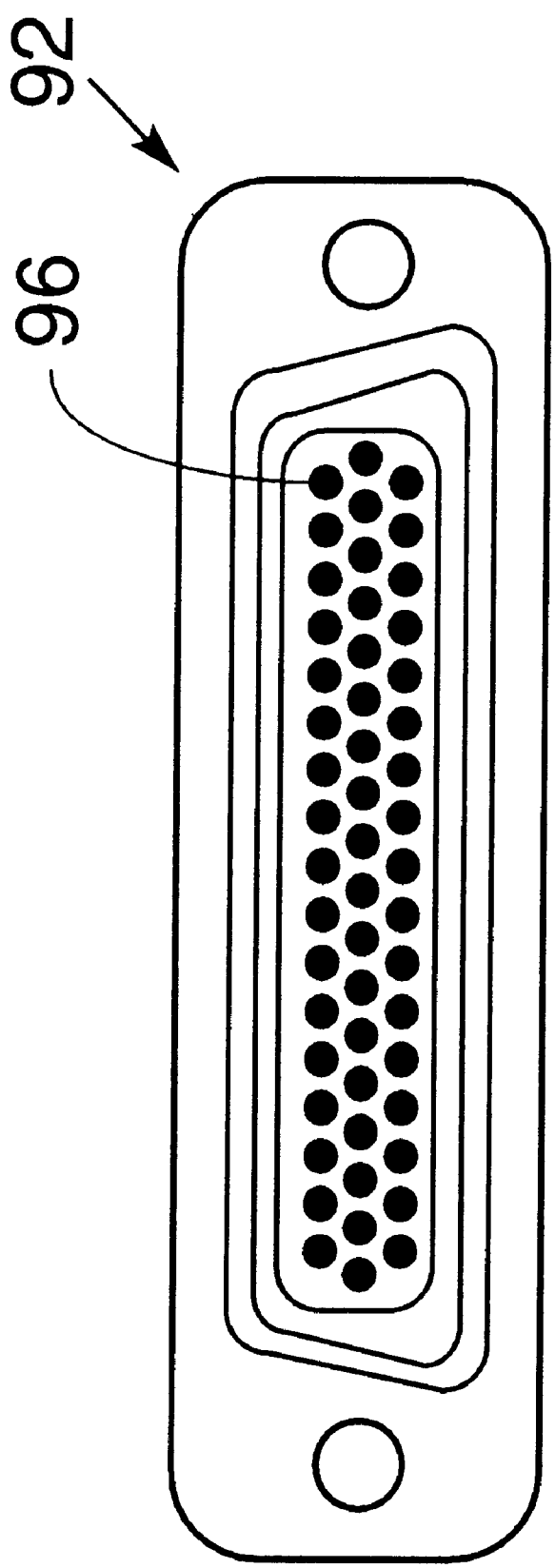
FIG. 6 is a front view of a female connector element of the modular fluid connector in FIG. 5.

As illustrated in FIG. 2, in the preferred embodiment of the present invention, modular connectors 90 provide fluid connection between the valve assembly 21 and various subassemblies of the dual manifold system. It will be apparent to one skilled in the art of connectors that myriad different modular connector designs are possible for use with the present invention. Referring now to FIG. 5, a preferred connector design will now be described. For the purpose of simplicity, the following discussion is directed specifically to a single modular connector located between aspiration manifold 10 and valve assembly 21. However, all of the modular connectors 90 can have similar structures and operate in a similar fashion. Modular connector 90 includes female and male components, 92 and 94, respectively. Channels 96 formed in female subconnector 92 are adapted for releasably engaging integral connector tips 95 extending from male component, or plug, 94. Preferably, the individual channels/fittings 96 of the female unit have integral sealing elements 99, such as ribs, for preventing the leakage of fluids passing through the connector. During operation of the assembly, male connector 94 is fitted in female connector 92 such that the ends of tips 95 contact integral stop mechanisms 98. The geometry of the connectors may vary. However, as illustrated in FIG. 6, the individual connector units are preferably designed much like a standard electrical connector.

In alternate embodiments of the present invention, auxiliary assembly features are included for improving registration and alignment of reagent samples dispensed on the target substrate and/or for improving quality control. For instance, in one alternate embodiment of the invention, fiducial pins and/or marks are integrated into the target substrate and/or microtiter plate. The integrated features can be directly sensed by a conventional vision system for ensuring proper alignment and orientation during operation. Alternatively, the integrated features can be designed for interaction with position-sensitive detection electronics. In a further embodiment of the present invention, detection means are provided for detecting the passage of a droplet of reagent from a dispense orifice 106. For instance, referring now to FIG. 7, photodiode 100 and photodetector 102 devices can be positioned proximate to a dispensing orifice 106 to sense the passage of a droplet. Alternatively, electronic conduction-based sensors can be incorporated directly into the dispense manifold, for example, by applying a conductive coating to portions of the inner wall of each orifice 106 and monitoring electrical current therebetween.

Referring now to FIGS. 1–7, the operation of the dual-manifold assembly of the present invention will now be described. Initially, a source plate 50, such as a microtiter plate, is advanced on a feeder track 70 until it is properly positioned beneath aspiration manifold 10, and target substrate 60 is advanced on track 72 until it is properly positioned beneath dispense manifold 20. An optional alignment step may be performed to ensure proper positioning and orientation of the source plate, the target substrate or both. With the source plate and aspiration manifold adequately aligned, aspiration manifold 10 is vertically-actuated until it is seated onto source plate 50 such that an air-tight seal is formed between the manifold 10 and the plate 50. In the preferred embodiment of the invention (FIG. 3), cap members 18 of the aspiration subassemblies form a seal over the reservoirs. Where the alternate embodiment of the aspiration manifold assembly is employed (FIG. 4), the aspiration manifold 10 is vertically-actuated until gasket 23 seals against the periphery of source plate 50. Preferably, during operation, the aspiration and dispense manifolds are limited to vertical movement.

With the aspiration manifold properly seated upon the source plate, pressure is introduced to the reservoirs from pressure source 40, via conduit(s) 12, to effect liquid transfer through conduits 14 toward dispense manifold 20. Preferably, once liquid transfer to the dispense manifold has been effected, switching valve 22 is actuated to disable fluid connection between the dispense manifold and the aspiration manifold, while enabling fluid communication between the dispense manifold and liquid ejection means 28. If necessary, dispense manifold 20 can be vertically positioned to a desired height above target substrate 60. Subsequently, a force, such as a pressure pulse, is communicated to the dispense manifold for a period of time to effect the ejection of a precise volume of liquid from the dispense manifold through orifices 106 to test sites 64 on target substrate 60. Preferably, the dispense manifold is maintained at a constant position during operation of the assembly.

Preferably, a complete array of test sites are printed contemporaneously, and tracks 70 and 72 are each advanced after the printing of a single array. However, liquid transferred from a single array of reservoirs may be adequate to dispense multiple arrays or sub-arrays of test sites. In that instance, printing can comprise repeatedly advancing test track 72 to reposition an array or sub-array of test sites beneath dispense manifold 20, while maintaining the position of feeder track 70. Conversely, other applications may require maintaining the position of test track 72 while advancing feeder track 70.

It will be apparent to one skilled in the art that further variations of the methods described herein are possible without departing from the scope of the invention. For instance, where track 70 and/or track 72 are adapted for movement in multiple directions, the method can include repositioning the reservoirs and/or test substrate via movement of the tracks 70, 72, such that the tracks are not "advanced". Similarly, where the printhead is adapted for being rotated, the step of positioning the dispense manifold can include the sub-step of rotating the printhead.

In an alternate embodiment of the present invention, the method includes the additional step of detecting the passage of a droplet, or volume, of liquid from the array of dispense manifold orifices to the array of test sites. In a further embodiment of the invention, the method includes periodically purging fluid transfer conduits of the assembly with a cleaning fluid such as water.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims. For instance, it will be apparent to one skilled in the art that various modifications to the preferred valving arrangement are possible.

We claim:

1. A dual-manifold assembly for transferring liquid from an array of reservoirs to an array of test sites on a target substrate, comprising:

a liquid aspiration manifold: a liquid dispense manifold having a plurality of orifices;

a plurality of conduits for providing fluid connection between said aspiration manifold and said dispense manifold;

a controllable pressure source for urging the liquid from said reservoirs through said plurality of conduits toward said dispense manifold;

a means for ejection of at least one droplet of said liquid, said ejection means mechanically or fluidicly connected to at least one of said plurality of orifices to eject said droplet onto at least one of said test sites, and a fluid switching valve disposed at or between an output of said dispense manifold and said aspiration manifold, said fluid switching valve for providing fluid connection between said fluid conduits and said dispense manifold to permit said liquids to be transferred to said dispense manifold.

2. A dual-manifold assembly as recited in claim 1, wherein said fluid switching mechanism is integrated into said liquid dispense manifold.

3. A dual-manifold assembly as recited in claim 1, wherein said ejection means is integrated into said liquid dispense manifold.

4. A dual-manifold assembly as recited in claim 1, further comprising at least one modular connector for providing fluid connection between lengths of said plurality of conduits.

5. A dual-manifold assembly as recited in claim 1, wherein said ejection means comprises an ink-jet printing valve incorporating drop-on-demand technology.

6. A dual-manifold assembly as recited in claim 5, wherein said ink-jet valve is one of a thermal ink-jet valve, a solenoid ink-jet valve, and a piezoelectric ink-jet valve.

7. A dual-manifold assembly as recited in claim 5, wherein said ink jet valve is adapted for delivering a pressure pulse having a pressure of about $6.9(10)^3$ N/m$^2$ to about $138(10)^3$ N/m$^2$, and having a pulse duration ranging from about $(10)^{-6}$ seconds to about $(10)^{-2}$ seconds.

8. A dual-manifold assembly as recited in claim 1, wherein said plurality of conduits comprise plastic tubing.

9. A dual-manifold assembly as recited in claim 1, wherein said plurality of conduits comprise at least one of metal and glass tubing.

10. A dual-manifold assembly as recited in claim 1, wherein said array of reservoirs comprise microtiter plate wells and said liquid comprises a reagent.

11. A dual-manifold assembly as recited in claim 1, wherein said array of test sites comprise biological sensors integrated on a microelectronic device.

12. A dual-manifold assembly as recited in claim 1, wherein the minimum distance between adjacent test sites on said target substrate is in the range of about 1 micron ($\mu$m) to about 10,000 microns ($\mu$m).

13. A dual-manifold assembly as recited in claim 1, wherein said liquid dispense manifold is adapted for dispensing volumes of liquid in the range of about $(10)^{-12}$ to about $(10)^{-6}$ liters.

14. A dual-manifold assembly as recited in claim 1, further comprising a conduit cleaning and purging apparatus.

15. A dual-manifold assembly as recited in claim 1, further comprising a means for detecting the passage of a droplet of liquid from a dispense manifold orifice.

16. A dual-manifold assembly as recited in claim 15, wherein said detection means comprise optoelectronic devices.

17. A dual-manifold assembly as recited in claim 15, wherein said detection means comprise electronic conduction-based sensors integrated into said dispense manifold.

18. A dual-manifold assembly as recited in claim 1, wherein said aspiration manifold assembly is adapted for being seated upon a source plate having an array of liquid-filled reservoirs, said aspiration manifold assembly comprising:

a base plate;

a gasket member disposed along the periphery of a lower surface of said base plate, said gasket dimensioned for sealing against a periphery of said source plate;

a pressure conduit extending through said base plate for pressurizing said array of liquid-filled reservoirs; and, a plurality of aspiration conduits extending through said base plate and into said liquid-filled reservoirs for aspirating said liquid from said reservoirs.

19. A dual-manifold assembly for transferring liquid from an array of reservoirs to an array of test sites on a target substrate, comprising:

a liquid aspiration manifold, wherein said aspiration manifold includes an array of aspiration subassemblies extending from a base plate and adapted for being received by said array of liquid-filled reservoirs, each subassembly comprising:

a guide member having a first end adapted for being mechanically fastened to said base plate and having a second flanged end extending away from said base plate;

a cap member having a first end adapted for engaging the flanged end of said guide member and a second end having a tapered outer surface for engaging the perimeter of one of said liquid-filled reservoirs; and, first and second conduits each extending through aligned apertures in said base plate, said guide member and said cap member;

wherein said first conduit terminates at a position above a liquid level of the reservoir and said second conduit terminates at a position below a liquid level of the reservoir, said first conduit providing a means for pressurizing said reservoir to urge liquid through said second conduit toward said dispense manifold;

a liquid dispense manifold having a plurality of orifices;

a plurality of conduits for providing fluid connection between said aspiration manifold and said dispense manifold;

a controllable pneumatic pressure source for urging the liquid from said reservoirs through said plurality of conduits toward said dispense manifold; and a means for effecting the ejection of at least one droplet of said liquid through at least one of said plurality of orifices and onto at least one of said test sites.

20. A dual-manifold assembly as recited in claim 19, wherein each of said guide member, said cap member and said base plate are integrated to form a unitary structure.

* * * * *